United States Patent [19]

Woessner et al.

[11] 4,029,698

[45] June 14, 1977

[54] CYCLOALKYLIDENOL ANALOGUES OF PROSTAGLANDINS E AND F

[75] Inventors: Warren Dexter Woessner; William Gerard Biddlecom; Henry Clifford Arndt, all of Madison; George Peter Peruzzotti, Middleton; Charles John Sih, Madison, all of Wis.

[73] Assignee: Miles Laboratories, Inc., Elkhart, Ind.

[22] Filed: Oct. 31, 1975

[21] Appl. No.: 627,627

Related U.S. Application Data

[60] Continuation-in-part of Ser. No. 436,221, Jan. 24, 1974, abandoned, which is a division of Ser. No. 383,670, July 30, 1973, abandoned.

[52] U.S. Cl. .................. 260/514 D; 260/438.1; 260/468 D; 260/586 R; 260/611 B; 260/617 R; 424/305; 424/317

[51] Int. Cl.$^2$ .................................. C07C 177/00

[58] Field of Search .................. 260/468 D, 514 D

[56] References Cited

FOREIGN PATENTS OR APPLICATIONS 7,410,185  2/1975  Netherlands .................. 260/408

*Primary Examiner*—Robert Gerstl
*Attorney, Agent, or Firm*—Myron B. Sokolowski

[57] ABSTRACT

Analogues of prostaglandins E and F, in which the $C_{15}$ hydroxyl group is incorporated into a cycloalkylidene moiety, stimulate smooth muscle.

1 Claim, No Drawings

CYCLOALKYLIDENOL ANALOGUES OF PROSTAGLANDINS E AND F

REFERENCE TO PRIOR APPLICATION

This is a continuation-in-part of U.S. Pat. application Ser. No. 436,221, filed on Jan. 24, 1974, which in turn is a division of U.S. Pat. application Ser. No. 383,670, filed on July 30, 1973; both prior applications are abandoned.

BACKGROUND OF THE INVENTION

Field of the Invention

The compounds of this invention are derivatives or analogues of a class of naturally occurring chemical compositions known as prostaglandins.

Natural prostaglandins are twenty-carbon atom alicyclic compounds related to prostanoic acid which is represented by the following structural formula:

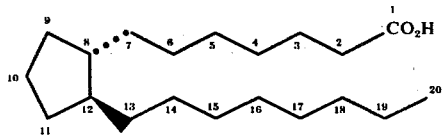

By convention, the carbon atoms of I are numbered sequentially from the carboxylic carbon atom. An important stereo-chemical feature of I is the trans-orientation of the side chains $C_1$–$C_7$ and $C_{13}$–$C_{20}$. In I, as elsewhere in this specification, a dotted line (...) indicates projection of the covalent bond below the plane of a reference carbon atom (the alpha-configuration), while a wedged line (◄) represents direction above said plane (the beta-configuration). These notations are applicable to all compounds hereinafter discussed.

The twelve natural prostaglandins which have been isolated to date have the structural formula:

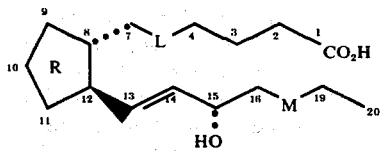

in which:
L and M may be ethylene or vinylene radicals; and, the five-membered ring may be

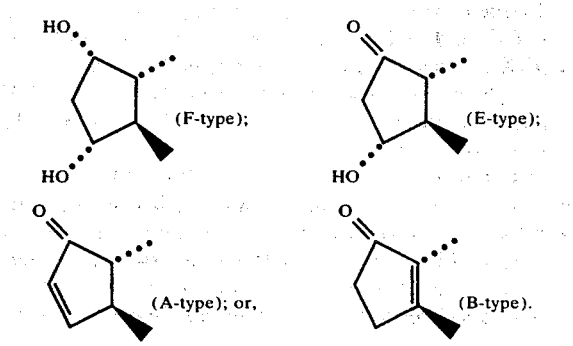

The natural prostaglandins represented by II, are classified according to the functional groups present in the five-membered ring structure and the presence of double bonds in the ring or chains. Prostaglandins of the F-class (PGF's) are characterized by α-oriented hydroxyl groups at $C_9$ and $C_{11}$; those of the E-type (PGE's) have a carbonyl group at $C_9$ and an α-oriented hydroxyl group at $C_{11}$; compounds of the A-series (PGA's) contain a carbonyl group at $C_9$ and a double bond at $C_{10}$ ($\Delta^{10,11}$); and members of the B-class (PGB's) have a carbonyl group at $C_9$ and an unsaturated bond between $C_8$ and $C_{12}$($\Delta^{8,12}$). Within each of the F, E, A, and B classes of prostaglandins are three subclassifications based upon the presence of double bonds in the side chains at $C_5$, $C_{13}$, or $C_{17}$. The presence of a trans-unsaturated bond only at $C_{13}$ is indicated by the subscript numeral 1; thus, for example, $PGE_1$ denotes a prostaglandin of the E-type (carbonyl at $C_9$ and an alpha-hydroxyl at $C_{11}$) with a trans-double bond at $C_{13}$. The presence of both a trans-double bond at $C_{13}$ and a cis-unsaturated bond at $C_5$ is denoted by the subscript numeral 2, for example, $PGE_2$. Lastly, a trans-double bond at $C_{13}$, a cis-double bond at $C_5$, and a cis-double bond at $C_{17}$ is indicated by the subscript numeral 3, for example, $PGE_3$. The above notations apply to prostaglandins of the A, B and F series as well, however, in the latter the alpha-orientation of the hydroxyl group at $C_9$ is indicated by the subscript Greek letter α after the numerical subscript. Thus $PGF_3 \alpha$ represents 9α,11α,15α-trihydroxy-5,17-cis, 13-trans-prostatrienoic acid (utilizing nomenclature based upon prostanoic acid).

It is important to note that in all natural prostaglandins there is an alpha-oriented hydroxyl group at $C_{15}$. In the Cahn-Ingold-Prelog system of defining stereochemistry, this $C_{15}$ hydroxyl group is in the S-configuration.

11-desoxy derivatives of PGE and PGF molecules do not occur as such in nature, but constitute a class of compounds which possess biological activity related to the parent compounds. Formula II represents 11-desoxy PGE's and PGF's when

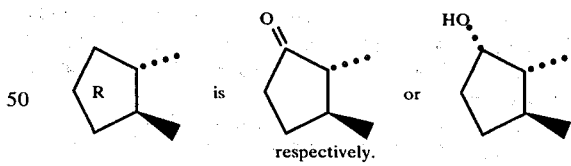

respectively.

I.U.P.A.C nomenclature of prostaglandins designates the carboxylic side chain as the parent compound: for example, $PGF_3 \alpha$ is 7-{3α, 5α-dihydroxy-2β-[(3S)-3-hydroxy-trans-1, cis-5-octenyl]-1α-cyclopentyl}-cis-5-heptenoic acid.

Recent research has indicated that the prostaglandins are ubiquitous in animal tissues and that prostaglandins, as well as analogues or derivatives thereof, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostaglandins are involved in the control of hormone synthesis and release in hormone-secreting glands. In rats, for example, $PGE_1$ and $PGE_2$ increases release of growth hormone while $PGA_1$ increases growth hormone synthesis. In sheep, $PGE_1$ and $PGF_{1\alpha}$ inhibit ovarian progesterone secretion. In a variety of mammals, $PGF_{1\alpha}$ and $PGF_{2\alpha}$ are implicated as luteolytic factors. In mice, $PGE_1$, $PGE_2$, $PGF_{1\alpha}$ and $PGE_1\beta$ increase thyroid activity. In hypophysectomized rats, $PGE_1$, $PGE_2$ and $PGF_{1\alpha}$ stimulate steroidogenesis in the adrenal glands.

In the mammalian male reproductive system, $PGE_1$ contracts the smooth muscle of the vas deferens. In the female reproductive system, PGE and $PGF\alpha$ compounds contract uterine smooth muscle. In general, PGE's, PGB's and PGA's relax in vitro human uterine muscle strips, while $PGF\alpha$'s contract such isolated preparations. PGE compounds in general promote fertility in the female reproductive system while $PGF_{2\alpha}$ has antifertility effects. $PGF_{2\alpha}$ also is believed to be involved in the mechanism of menstruation. In general, $PGE_2$ exerts potent oxytocic effects in inducing labor, while $PGF_{2\alpha}$ induces spontaneous abortions in early pregnancy.

$PGF\alpha$'s and PGE's have been isolated from a variety of nervous tissue and they have been postulated to serve a neurotransmitter role. $PGE_1$ retards whereas $PGF_{2\alpha}$ facilitates transmission in motor pathways in the CNS. It has been reported that $PGE_1$ and $PGE_2$ inhibit transmitter release from adrenergic nerve endings in the guinea pig.

Prostaglandins stimulate contraction of gastrointestinal smooth muscle in vivo and in vitro. In dogs, $PGA_1$, $PGE_1$ and $PGE_2$ inhibit gastric secretion. $PGA_1$ exhibits similar activity in man.

In most mammalian respiratory tracts, PGE's and $PGF\alpha$'s relax in vitro preparations, $PGE_1$ and $PGE_2$ relax human smooth muscle while $PGF_{2\alpha}$ contracts such preparations. PGE and PGF compounds are normally found in the human lung, and it has been postulated that some cases of bronchial asthma involve an imbalance in the production or metabolism of those compounds.

Prostaglandins have been shown to be involved in certain hematic mechanisms in mammals. $PGE_1$, for example, inhibits thrombogenesis in vitro through its effects on blood platelets.

In a variety of mammalian cardiovascular systems, PGE's and PGA's are vasodilators whereas $PGF\alpha$'s are vasoconstrictors, by virtue of their action on vascular smooth muscle.

Prostaglandins are naturally found in the kidney and reverse experimental and clinical renoprival hypertension.

The clinical implications of prostaglandins and derivatives or analogues thereof are far-ranging and include, but are not limited to the following: in obstetrics and gynecology, they may be useful in fertility control, treatment of menstrual disorders, induction of labor, and hormone disorders; in gastroenterology, they may be useful in the treatment of peptic ulcers, and various disorders involving motility, secretion, and absorption in the gastrointestinal tract; in the respiratory area, they may be beneficial in the therapy of bronchial asthma and other diseases involving bronchoconstriction; in hematology, they may have utility as anti-clotting agents in diseases such as venous thrombosis, thrombotic coronary occlusion and other diseases involving thrombi; in circulatory diseases they may have therapeutic utility in hypertension, peripheral vasopathies, and cardiac disorders.

In general, the natural prostaglandins affect smooth muscle regardless of origin in mammalian systems both in vivo and in vitro. This activity allows a rapid bioassay of prostaglandin derivatives or analogues by use of isolated muscle strips in vitro. (Cf. Bergstrom et al., Pharmacol. Rev., 20: 1 [1968]; Ferreira and Vane, Nature, 216: 868 [1961]).

The field to which this invention pertains is discussed in the following references: *The Prostaglandins, Vol. I.*, P. Ramwell, Ed., New York, Plenum Press, 1973; Ann. N.Y. Acad. Sci., 180: 1–568 (1971); and Higgins and Braunwald, J. Am. Med. Assn., 53: 92–112 (1972).

SUMMARY

Prostaglandin analogues having the following structural formula III constitute the subject matter of this invention:

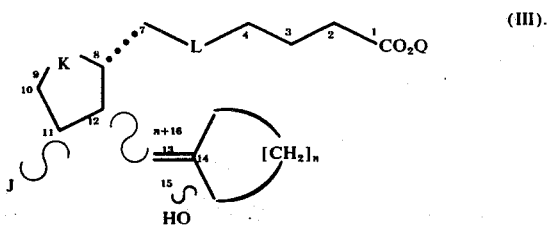

In formula III: J is hydrogen or hydroxyl; K is carbonyl or carbinol; L is ethylene of vinylene; Q is hydrogen, loweralkyl of 1 to 3 carbon atoms, or a pharmacologically acceptable nontoxic cation; and $n$ is an integer having a value of from 2 to 6 such that there exists between $C_{15}$ and $C_{n+16}$ an alkylene bridge of $n$ methylene groups. In III: carbon atoms are numbered sequentially as indicated, following the conventional practice utilized in prostaglandin chemistry; a dotted line (•••) represents a covalent bond projecting below the plane of a reference carbon atom (alpha-configuration) while a wedged line (◂) indicates a covalent bond protruding above said reference plane (beta-configuration); and a swung dash or serpentine line (∽) denotes a covalent bond which can be in either the alpha- or beta-configuration. In III, when the covalent bond at $C_7$–$C_8$ is in the alpha-configuration and the bond $C_{12}$–$C_{13}$ is in the beta-configuration, the prefix "nat-" is used before the compound name to describe this trans-orientation of the side-chains; however, the reverse case, i.e. when $C_7$–$C_8$ is in the beta- and $C_{12}$–$C_{13}$ is in the alpha-configuration, the prefix "ent-" is used before the compound name. Analogues or derivatives of $PGE_1$ and $PGE_2$ are represented by formula III in the case where J is hydroxyl, K is carbonyl, and L respectively is ethylene or vinylene; similarly, analogues or derivatives of $PGF_1$ and $PGF_2$ are represented in the case where J and K are hydroxyl and L respectively is ethylene or ethenylene. Corresponding 11-desoxy-PGE and -PGF analogues or derivatives are indicated by both formulas when J is hydrogen.

An important structural feature of III is the presence of the unsaturated bond at $C_{13}$ and the hydroxyl substituent at $C_{15}$ both of which are common to all natural prostaglandins. Unlike the latter, however, analogues with structure III contain the $C_{13}$ and the $C_{15}$ atoms in a cyclo alkylidene structure wherein the $C_{15}$ atom is incorporated into an $n + 3$ carbon atom ring. In structure III, $C_{15}$ is the second atom in the ring.

The following are illustrative examples of formula III:

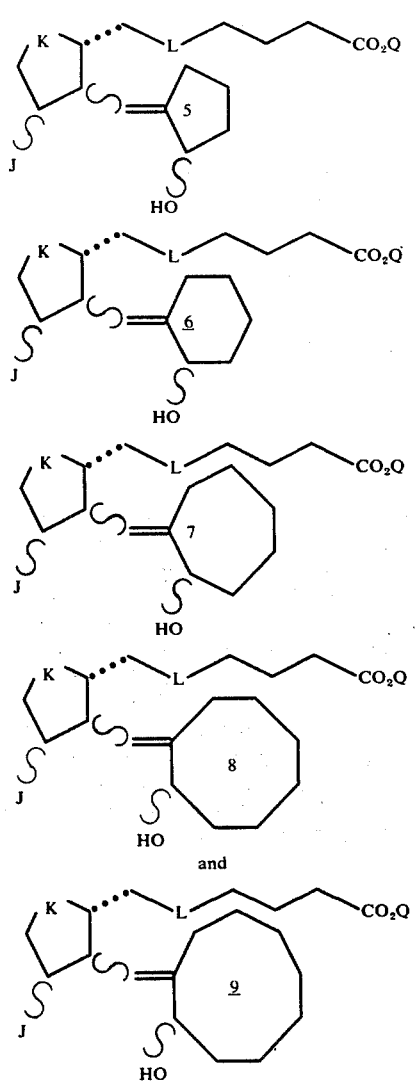

Compounds having formula III are prepared according to the synthesis reported by Sih et al. (J. Am. Chem. Soc., 95: 1676 [1973]), outlined in Table A. In the reaction sequences depicted in Table A, t-butyl-lithium (V), is commercially available or easily prepared according to methods which are well known in organic chemistry. Hexamethylphosphorous triamide copper iodide, VI, is prepared as follows: (1) add 18.39 g of purified CuI (Inorg. Synth., 7: 9 [1963]) to 177 g KI in 135 ml. $H_2O$ and stir with activated charcoal (Norite); (2) filter the solution through infusorial earth (Celite) and add 14.5 g (0.089 mole) of hexamethylphosphorous triamide (commercially available) under argon atmosphere; (3) filter, wash with aqueous KI and $H_2O$; (4) dissolve product in dry ether, filter, remove ether in vacuo to obtain 13.85 g hexamethyl-phosphorous triamide copper (I) iodide NMR ($COCl_3$): singlet, $\delta$ 2.65. Compound VII can be prepared from 2-(6-carbomethoxyhexyl)cyclopentane-1,3,4-trione (Cf. Katsube and Matsui; Agr. Biol. Chem., 33: 1078 [1969] for the synthesis of this compound) as described in the referenced Sih et al. publication. Examples of VIII which are employed in the synthesis of III and IV include:

2-(6-carbomethoxyhexyl)-4-hydroxy-2-cyclopenten-1-one;
2-(6'-carbomethoxy-cis-2'-hexenyl)-4-hydroxy-2-cyclopenten-1-one;
2-(6'-carbomethoxy-hexyl)-2-cyclopenten-1-one; and
2-(6'-carbomethoxy-cis-2'-hexenyl)-2-cyclopenten-1-one.

Compounds IV of Table A are synthesized according to the process reported by W. R. Benson and A. E. Pohland (J. Org. Chem., 29: 385 [1964]):

TABLE A

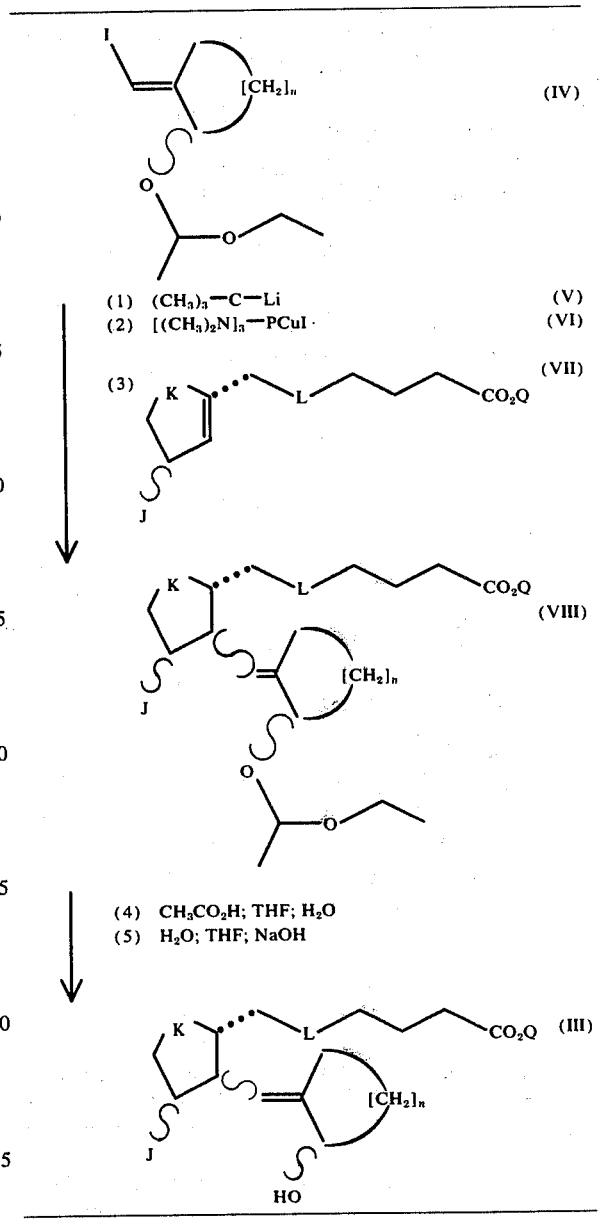

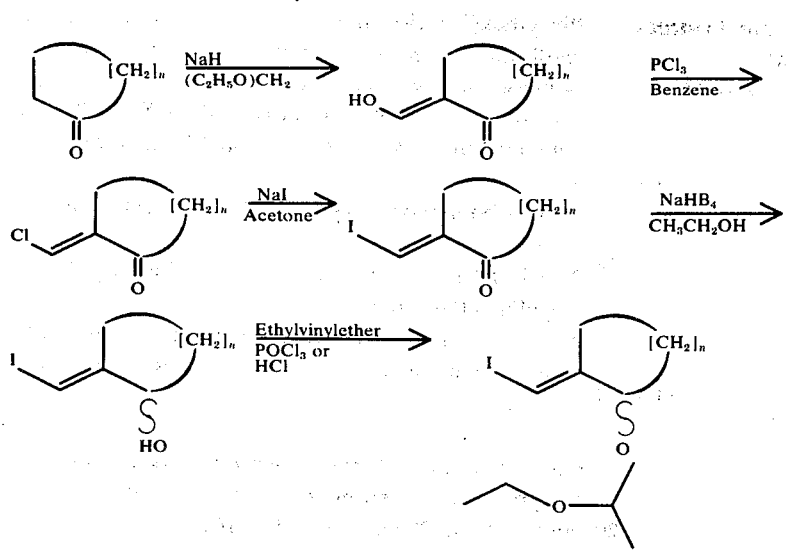

As defined in formula III, n has a value of from 2 to 6. Examples of intermediates IV utilized in the reaction IV → III include the following:

1-ethoxyethoxy-2-(2'-iodo-methylidene)-cyclopentane;
1-ethoxyethoxy-2-(2'-iodo-methylidene)-cyclohexane;
1-ethoxyethoxy-2-(2'-iodo-methylidene)-cycloheptane; and
1-ethoxyethoxy-2-(2'-iodo-methylidene)-octane.

Steps 4 and 5 in Table A involve removal of the ethoxyethoxy group and methyl ester group, respectively.

In compounds having formula III, K can be converted from a carbonyl group to a carbinol group by reaction with $NaHB_4$ in methanol.

Sodium or potassium salts of III can be prepared by known procedures.

The compounds represented by III are useful analogues of natural E- and F- prostaglandins and stimulate in vitro smooth muscle preparations derived from a variety of tissues and organs of experimental animals. Such in vitro smooth muscle assays are widely utilized to determine the activity of natural prostaglandins as well as prostaglandin analogues (Bundy et al., Ann. N.Y. Acad. Sci., 180: 76 [1961]; Bergstrom et al., Pharmacol. Revs., 20: 1 [1968]). Details of the activity of certain compounds having formula III are presented in Example 2, below.

Compounds III inhibit aggregation of human platelets in vivo and exhibit useful cardiovascular properties, as demonstrated in Example 3, below.

DESCRIPTION OF THE PREFERRED EMBODIMENTS

EXAMPLE 1

A.
2-(6'-Carboxyhexyl)-3-(2''-Anti-Hydroxymethylidenecycloheptyl)-Cyclopentanone 2.14 g (6.69 mmol) of 1-ethoxyethoxy-2-(2'-iodoethylidene)-cycloheptane was dissolved in 40 ml anhydrous ether, cooled to −78° C., and stirred under argon atmosphere. 11.0 ml of 1.23 M t-butyllithium in pentane was added and the mixture was stirred for 3 hours at −78° C. The reaction mixture was then added to a complex formed by dissolving 0.873 mg copper (I) pentyne in 23 ml ether with 2.43 ml of hexamethylphosphorous triamide. The mixture was stirred at −78° C. resulting in an orange solution. 1.34 g (6.0 mmol) of 2-(6'-carbomethoxyhexyl)-2-cyclopenten-1-one in 23 ml of ether was added, the mixture was stirred for 15 min. at −78° C., and brought to 0° C. by means of an ice-salt bath over an interval of 1.5 hr. The mixture was stirred for 0.5 hr. at 0° C. and an additional 0.5 hr. at 25° C. The mixture was processed with 20% aqueous $(NH_4)_2SO_4$, 2% (V/V) $2H_2SO_4/H_2O$, saturated aqueous $NaHCO_3$, saturated aqueous NaCl, filtered and stripped in vacuo to yield 2.10 g of a green oil. NMR ($CDCl_3$) analysis afforded the following data: δ 3.65, singlet, $CO_2CH_3$; δ 4.70, multiplet,

δ 5.32, doublet,

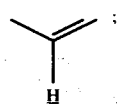

$J_{12-13} = 9$ Hz. The exthoxyethoxy group was removed by reacting the product with 48 ml of 65/35 acetic acid/water and 4.8 ml of tetrahydrofuran (THF) for 15 hrs. at 25° C. The product was processed with 20% $(NH_4)_2SO_4$, 2% (V/V) $H_2SO_4$, saturated aqueous $NaHCO_3$, saturated aqueous NaCl, filtered and stripped in vacuo to yield 1.81 g of a yellow oil. NMR ($CDCl_3$) showed no absorption at δ 4.70. The methyl ester was hydrolyzed by reaction with 20 ml THF and 20 ml 1N NaOH for 18 hrs. at 25° C. The product was processed as described above to obtain 1.44 g of a clear orange oil, 2-(6'-carboxyhexyl)-3-(2''-anti-hydroxymethylidene-cycloheptyl)-cyclopentanone.

Analysis: IR: $\lambda_{max}^{CHCl}$ 2.78μ, 5.75μ, 5.85μ; MS: 336.318; NMR($COCl_3$): δ 5.40, doublet, 1H, $C_{13}$-H; $J_{12,13} = 9.0$ Hz; δ 4.35, multiplet, 1H, CHOH; δ 7.86, broad singlet, 2H, $CO_2H$, —OH;

B. Substitution of 1-ethoxyethoxy-2-(2'-iodo-ethylidene-cyclopropane, -cyclobutane, -cyclopentane, -cyclohexane, cyclooctane, or cyclononane in the above procedure yields the following 11-desoxy-$PGE_1$ analogues:

1. 2-(6'-carboxyhexane)-3-(2''-anti-hydroxy-methylidene-cyclopentyl)-cyclopentanone;
2. 2-(6'-carboxyhexane)-3-(2''-anti-hydroxy-methylidene-cyclohexyl)-cyclopentanone;
3. 2-(6'-carboxyhexane)-3-(2''-anti-hydroxy-methylidene-cyclooctyl)-cyclopentanone; and,
4. 2-(6'-carboxyhexane)-3-(2''-anti-hydroxy-methylidene-cyclononyl)-cyclopentanone.

C. Substitution of 2-(6'-carbomethoxy-cis-2'-hexene)-2-cyclopenten-1-one for the corresponding 2-(6'-carbomethoxy-hexane)-2-cyclopenten-1-one in procedures A and B results in the following 11-desoxy-$PGE_2$ analogues:

1. 2-(6'-carboxy-cis-2'-hexene)-3-(2''-anti-hydroxy-methylidene-cyclopentyl)-cyclopentanone;
2. 2-(6'-carboxy-cis-2'-hexene)-3-(2''-anti-hydroxy-methylidene-cyclohexyl)-cyclopentanone;
3. 2-(6'-carboxy-cis-2'-hexene)-3-(2''-anti-hydroxy-methylidene-cycloheptyl)-cyclopentanone;
4. 2-(6'-carboxy-cis-2'-hexene)-3-(2''-anti-hydroxy-methylidene-cyclooctyl)-cyclopentanone; and,
5. 2(6'-carboxy-cis-2'-hexene)-3-(2''-anti-hydroxy-methylidene-cyclononyl)-cyclopentanone.

D. Substitution of 2-(6'-carbomethoxyhexane)-4-hydroxy-2-cyclopenten-1-one or 2-(6'-carboxymethyl-cis-2'-hexene)-4-hydroxy-2-cyclopenten-1-one in procedures A and B yields the following $PGE_1$ and $PGE_2$ derivatives, respectively:

1. 2-(6'-carbomethoxyhexane)-3-(2''-anti-hydroxy-methylidene-cyclopentyl)-4-hydroxy-2-cyclopenten-1-one;
2. 2-(6'-carbomethoxyhexane)-3-(2''-anti-hydroxy-methylidene-cyclohexyl)-4-hydroxy-2-cyclopenten-1-one;
3. 2-(6'-carbomethoxyhexane)-3-(2''-anti-hydroxy-methylidene-cycloheptyl)-4-hydroxy-2-cyclopenten-1-one;
4. 2-(6'-carbomethoxyhexane)-3-(2''-anti-hydroxy-methylidene-cyclooctyl)-4-hydroxy-2-cyclopenten-1-one;
5. 2-(6'-carbomethoxyhexane)-3-(2''-anti-hydroxy-methylidene-cyclononyl)-4-hydroxy-2-cyclopenten-1-one;
6. 2-(6'-carbomethoxy-cis-2'-hexene)-3-(2''-anti-hydroxy-methylidene-cyclopentyl)-4-hydroxy-2-cyclopenten-1-one;
7. 2-(6'-carbomethoxy-cis-2'-hexene)-3-(2''-anti-hydroxy-methylidene-cyclohexyl)-4-hydroxy-2-cyclopenten-1-one;
8. 2-(6'-carbomethoxy-cis-2'-hexene)-3-(2''-anti-hydroxy-methylidene-cycloheptyl)-4-hydroxy-2-cyclopenten-1-one;
9. 2-(6'-carbomethoxy-cis-2'-hexene)-3-(2''-anti-hydroxy-methylidene-cyclooctyl)-4-hydroxy-2-cyclopenten-1-one; and
10. 2-(6'-carbomethoxy-cis-2'-hexene)-3-(2''-anti-hydroxy-methylidene-cyclononyl)-4-hydroxy-2-cyclopenten-1-one.

E. Hydride reduction of the $PGE_1$, $PGE_2$, 11-desoxy-$PGE_1$, and 11-desoxy-$PGE_2$ analogues described in Sections B, C, and D, above, yield the corresponding $PGF_1$, $PGF_2$, 11-desoxy-$PGF_1$ and 11-desoxy-$PGF_2$ analogues, respectively:

1. 1-hydroxy-2-(6'-carbomethoxyhexane)-3-(2''-anti-hydroxy-methylidene-cyclopentyl)-cyclopentane;
2. 1-hydroxy-2-(6'-carbomethoxyhexane)-3-(2''-anti-hydroxy-methylidene-cyclohexyl)-cyclopentane;
3. 1-hydroxy-2-(6'-carbomethoxyhexane)-3-(2''-anti-hydroxy-methylidene-cycloheptyl)-cyclopentane;
4. 1-hydroxy-2-(6'-carbomethoxyhexene)-3-(2''-anti-hydroxy-methylidene-cyclooctyl)-cyclopentane;
5. 1-hydroxy-2-(6'-carbomethoxyhexane)-3-(2''-anti-hydroxy-methylidene-cyclononyl)-cyclopentane;
6. 1-hydroxy-2-(6'-carbomethoxyhexene)-3-(2''-anti-hydroxy-methylidene-cyclopentyl)-cyclopentant;
7. 1-hydroxy-2-(6'-carbomethoxyhexene)-3-(2''-anti-hydroxy-methylidene-cyclohexyl)-cyclopentane;
8. 1-hydroxy-2-(6'-carbomethoxyhexene)-3-(2''-anti-hydroxy-methylidene-cycloheptyl)-cyclopentane;
9. 1-hydroxy-2-(6'-carbomethoxyhexene)-3-(2''-anti-hydroxy-methylidene-cyclooctyl)-cyclopentane;
10. 1-hydroxy-2-(6'-carbomethoxyhexene)-3-(2''-anti-hydroxy-methylidene-cyclononyl)-cyclopentane;
11. 1,4-di-hydroxy-2-(6'-carbomethoxyhexane)-3-(2''-anti-hydroxy-methylidene-cyclopentylidene-methyl)-cyclopentane;
12. 1,4-di-hydroxy-2-(6'-carbomethoxyhexane)-3-(2''-anti-hydroxy-methylidene-cyclohexylidene-methyl)-cyclopentane;
13. 1,4-di-hydroxy-2-(6'-carbomethoxyhexane)-3-(2''-anti-hydroxy-methylidene-cycloheptylidene-methyl)-cyclopentane;
14. 1,4-di-hydroxy-2-(6'-carbomethoxyhexane)-3-(2''-anti-hydroxy-methylidene-cyclooctylidene-methyl)-cyclopentane;
15. 1,4-di-hydroxy-2-(6'-carbomethoxyhexane)-3-(2''-anti-hydroxy-methylidene-cyclononylidene-methyl)-cyclopentane;
16. 1,4-di-hydroxy-2-(6'-carbomethoxyhexene-2-(6'-carbomethoxyhexene)-3-(2''-anti-hydroxy-methylidene-cyclopentylidene-methyl)-cyclopentane;
17. 1,4-di-hydroxy-2-(6'-carbomethoxyhexene)-3-(2''-anti-hydroxy-methylidene-cyclohexylidene-methyl)-cyclopentane;
18. 1,4-di-hydroxy-2-(6'-carbomethoxyhexene)-3-(2''-anti-hydroxy-methylidene-cycloheptylidene-methyl)-cyclopentane;
19. 1,4-di-hydroxy-2-(6'-carbomethoxyhexene)-3-(2''-anti-hydroxy-methylidene-cyclooctylidene-methyl)-cyclopentane; and,
20. 1,4-di-hydroxy-2-(6'-carbomethoxyhexene)-3-(2''-anti-hydroxy-methylidene-cyclononylidene-methyl)-cyclopentane.

EXAMPLE 2

Prostaglandin Activity in the Cascade Assay System

The superfusion technique introduced by Gaddum (Brit. J. Pharmacol., 6: 321 [1953]) consists of dropwise bathing an isolated tissue with a nutrient solution, instead of submersing it in a chamber filled with the fluid. This procedure allows a greater sensitivity for biological assays, since test compounds are less diluted than in usual systems. An additional advantage is that a compound can be tested simultaneously in several structures by arranging the tissues in vertical succession to allow successive contact with the test material. This procedure has been called the cascade system and has been specially useful for determination of prostaglandin activity (Ferreira and Vane, Nature, 216, 868 [1967]); (Bergstrom et al., Pharmacol. Rev., 20: 1 [1968]).

A. Preparation of Tissues

Rat stomach fundus

After sacrifice of the animal, the stomach was removed, the antrum cut transversely and the fundus cut in order to preserve the longitudinal muscle as described by Vane (Brit. J. Pharmacol., 12: 344 [1959]).

Superfusion fluid

Krebs bicarbonte solution bubbled with a mixture of 95% $O_2$ and 5% $CO_2$ at a temperature of 37° C. was applied dropwise over the preparations at a rate of 10 ml/min. The following antagonists were added to the solution: atropine (0.1 mcg/ml), phenoxy-benzamine (0.1 mcg/ml), propranolol (3.0 mcg/ml), methysergide (0.2 mcg/ml) and brompheniramine (0.1 mcg/ml). The use of these antagonists in the nutrient eliminated the possibility of smooth muscle responses due to stimulation of cholinergic, adrenergic, serotonin or histamine receptors.

Test drugs

Prostaglandin derivatives were diluted in order to administer concentrations ranging from 0.001 ng to 100 mcg. Concentrations were applied dropwise in a 0.5 ml-volume.

B. Results

Results of the cascade assay in the rat stomach fundus are shown in Table B for the following compound: 2-(6'-carboxyhexyl)-3-(2''-anti-hydroxycycloheptylidenemethyl)-cyclopentanone. In Table B, a zero indicates no activity at the concentration tested. For comparison purposes, $PGE_1$ at a concentration of 31 ng produced 4.0 g of tension in the rat stomach fundus preparation.

TABLE B

| TENSION (grams) | DOSE (micrograms) |
|---|---|
| 0 | 0.01 |
| 0.6 | 0.10 |
| 1.0 | 1.0 |
| 2.1 | 10.0 |
| 3.3 | 100.0 |

EXAMPLE 3

A. Evaluation of Inhibition of Human Platelet Aggregation by Analogues of Prostaglandins Human Structure III The ability of test compounds to inhibit platelet aggregation was determined by a modification of the turbidometric technique of Born (Nature, 194: 927 ([1962). Blood was collected from human volunteers who had not ingested aspirin or aspirin-containing products within the preceding two weeks in heparinized containers and was allowed to settle for 1 hour. The platelet rich plasma (PRP) supernates were collected and pooled. Siliconized glassware was used throughout.

In a representative assay 1.9 ml of PRP and 0.2 ml of test compound at the appropriate concentration (0.001 to 100 mcgm), or 0.2 ml of distilled water (control procedure) were placed in sample cuvettes. The cuvettes were placed in a 37° C incubation block for 15 minutes, and then in a spectrophotometer linked to a strip chart recorder. After 30–60 seconds, 0.2 ml of a solution, prepared by diluting a calf-skin collagen solution 1:9 with Tyrodes' Solution, was added to each cuvettes. Platelet aggregation was evidenced by a decrease in optical density.

Calculation of the degree of inhibition of platelet aggregation exhibited by each concentration of test compound was accomplished according to the method of Caprino et al., (Arzneim-Forsch., 23: 1277 [1973]). An $ED_{50}$ value was then determined graphically, 2-(6'-Carboxyhexyl)-3-(2''-anti-hydroxy-cycloheptylidenemethyl)cyclopentanone has an $ED_{50}$ of 18.0 mcg/kg.

B. Evaluation of the Effects of Prostaglandin Analogues III on Femoral Blood Flow in the Dog The peripheral vasodilator or constrictor effects of test compounds ere determined in mongrel dogs of either sex, weighing between 10 and 20 kg anesthetized intraveneously with 35 mg/kg of sodium pentobarbital. An external iliac artery was dissected immediately above the femoral arch for a length of approximately 5 cm and a previously calibrated, non-connulating electromagnetic flowmeter sensor with a lumen between 2.5 and 3.5 mm was placed snugly aroung the vessel. Cannulas were placed in a branch of the artery arising distally to the location of the flowmeter sensor for intraarterial drug administrations, in the contralateral femoral artery for systemic blood pressures recordings and in the tracea for artificial respiration with room air. Femoral blood flow and systemic blood pressure were continuously recorded with an electromagnetic flowmeter and pressure transducer, respectively.

After an adequate control period, test compounds were injected intraareterially at one log-spaced doses ranging from 0.001 to 10 mcg., in a volume of 0.5 ml and at 5 to 10 minute intervals. Maximum changes in bloodflow, as well as any variations in blood pressure, were tabulated for each dose in absolute values (ml/min. and mmHg). The calculations were made taking as control values those existing immediately before administration of each dose. The direction of the observed change (plus for increase and minus for decrease) was also noted. The dose changing bloodflow by 100 ml/min ($ED_{100}$ ml/min.) was calculated graphically. 2'-(6'-Carboxyhexyl)-3-(2''-anti-hydroxy-cycloheptylidenemethyl)-cyclopentanone has an $ED_{50}$ of 0.63 mcg/kg.

What is claimed is:
1. 2-(6'-Carboxyhexyl)-3-(2''-anti-hydroxycycloheptylidenemethyl)-cyclopentanone.

* * * * *

UNITED STATES PATENT AND TRADEMARK OFFICE
CERTIFICATE OF CORRECTION

PATENT NO. : 4,029,698
DATED : June 14, 1977
INVENTOR(S) : Warren Dexter Woessner et al It is certified that error appears in the above-identified patent and that said Letters Patent are hereby corrected as shown below:

Column 3, Line 36, After "in vitro" insert -- preparation of tracheal smooth muscle. In in vitro --.

Column 10, Line 43, After "hydroxy", delete "-2-(6'-carbomethoxy-hexene".

Column 12, Line 28, Change "ere" to -- were --.

Signed and Sealed this

Fifteenth Day of August 1978

[SEAL]

Attest:

RUTH C. MASON
Attesting Officer

DONALD W. BANNER
Commissioner of Patents and Trademarks